(12) United States Patent
Engelbart et al.

(10) Patent No.: US 9,027,621 B2
(45) Date of Patent: *May 12, 2015

(54) VISION INSPECTION DURING APPLICATION OF COMPOSITE TAPE

(71) Applicant: The Boeing Company, Chicago, IL (US)

(72) Inventors: Roger W. Engelbart, St. Louis, MO (US); Reed E. Hannebaum, Belleville, IL (US); Timothy Pollock, Ballwin, MO (US)

(73) Assignee: The Boeing Company, Chicago, IL (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/154,255

(22) Filed: Jan. 14, 2014

(65) Prior Publication Data

US 2014/0124142 A1    May 8, 2014

Related U.S. Application Data

(62) Division of application No. 11/202,411, filed on Aug. 11, 2005, now Pat. No. 8,668,793.

(51) Int. Cl.
*B32B 41/00* (2006.01)
*B29C 70/32* (2006.01)
*B29C 70/38* (2006.01)
*B29C 70/54* (2006.01)
*B29L 31/30* (2006.01)
*G01N 21/84* (2006.01)

(52) U.S. Cl.
CPC .............. *B32B 41/00* (2013.01); *B29C 70/32* (2013.01); *B29C 70/386* (2013.01); *B29C 70/541* (2013.01); *B29L 2031/3076* (2013.01); *G01N 2021/8472* (2013.01)

(58) Field of Classification Search
CPC ..................................................... B32B 41/00
USPC .................................. 156/350, 378, 64, 379
See application file for complete search history.

(56) References Cited

U.S. PATENT DOCUMENTS 7,372,556 B2 *    5/2008    Engelbart et al. .......... 356/237.1

* cited by examiner

*Primary Examiner* — Daniel Lee

(57) ABSTRACT

A system comprises a feed assembly for applying composite tape; a unit for forming lateral stripes across a portion of the tape that has been applied; a camera for capturing images of the lateral stripes; and a processor programmed to process the images of the lateral stripes to identify any discontinuities in the tape. Those stripes intersecting any discontinuities will make those discontinuities apparent.

20 Claims, 10 Drawing Sheets

US 9,027,621 B2

VISION INSPECTION DURING APPLICATION OF COMPOSITE TAPE

This is a division of U.S. Ser. No. 11/202,411 filed 11 Aug. 2005, now U.S. Pat. No. 8,668,793.

BACKGROUND

Fabrication of a composite structure may include progressively building up a plurality of layers of thin composite tape or tow. For instance, a tape placement head of a manufacturing system moves over the surface of a template and deposits tapes of composite material onto the template.

Irregularities in the deposited tape may be detected by an automatic monitoring system. During detection, a portion of the tape on the workpiece is illuminated, and images of the illuminated portion are processed to determine whether the deposited tape has any irregularities. Irregularities may include discontinuities (e.g., gaps) between a recently-applied portion of tape and a previously-applied portion of tape.

The image processing may include edge detection and analysis. Such image processing is intensive.

SUMMARY

According to an embodiment herein, a system comprises a feed assembly for applying composite tape; a unit for forming lateral stripes across a portion of the tape that has been applied; a camera for capturing images of the lateral stripes; and a processor programmed to process the images of the lateral stripes to identify any discontinuities in the tape. Those stripes intersecting any discontinuities will make those discontinuities apparent.

According to another embodiment herein, a tape lamination machine comprises a forming tool; and a plurality of head assemblies for depositing composite tape on the forming tool. Each head assembly includes a feed assembly for applying composite tape, a unit for forming lateral stripes across a portion of the tape that has been applied, a camera for capturing images of the lateral stripes, and a processor programmed to process the images of the stripes to identify any discontinuities in the tape. Those stripes intersecting any discontinuities will make those discontinuities apparent.

These features and functions may be achieved independently in various embodiments or may be combined in other embodiments. Further details of the embodiments can be seen with reference to the following description and drawings.

DETAILED DESCRIPTION

Figure 1:
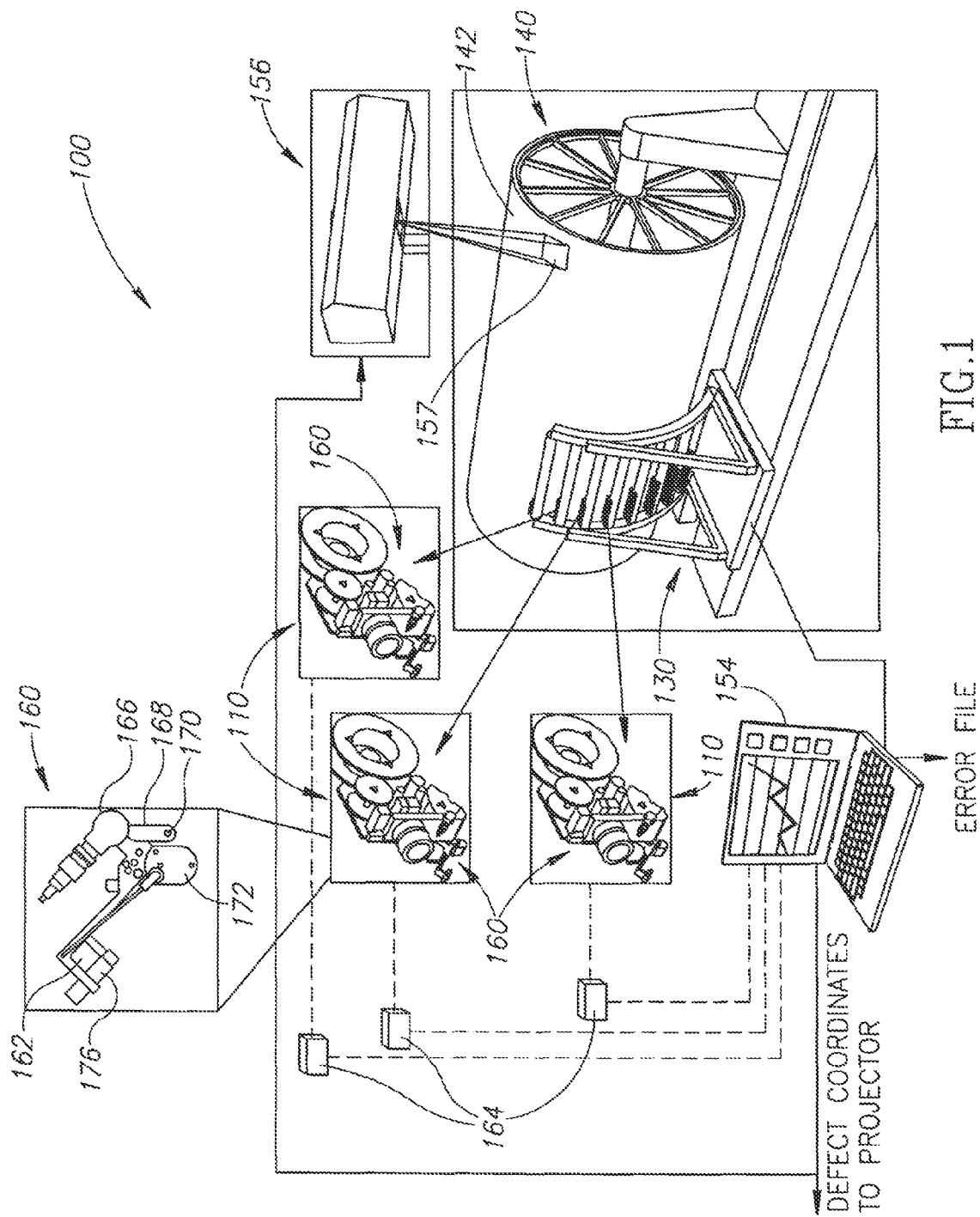
FIG. 1 is an illustration of a system for manufacturing composite components.

FIG. 1 illustrates a system 100 for manufacturing composite components. The system 100 includes a plurality of head assemblies 110 coupled to a translation platform 130 and operatively positioned proximate a forming tool (or template) 140. The translation platform 130 is adapted to systematically move the head assemblies 110 along translation paths (e.g. three-dimensional paths) proximate the forming tool 140, and each head assembly 110 is adapted to perform placement and consolidation of a fiber-reinforced composite tape material onto the forming tool 140 to produce a laminated composite workpiece 142, as described more fully below.

Figure 2:
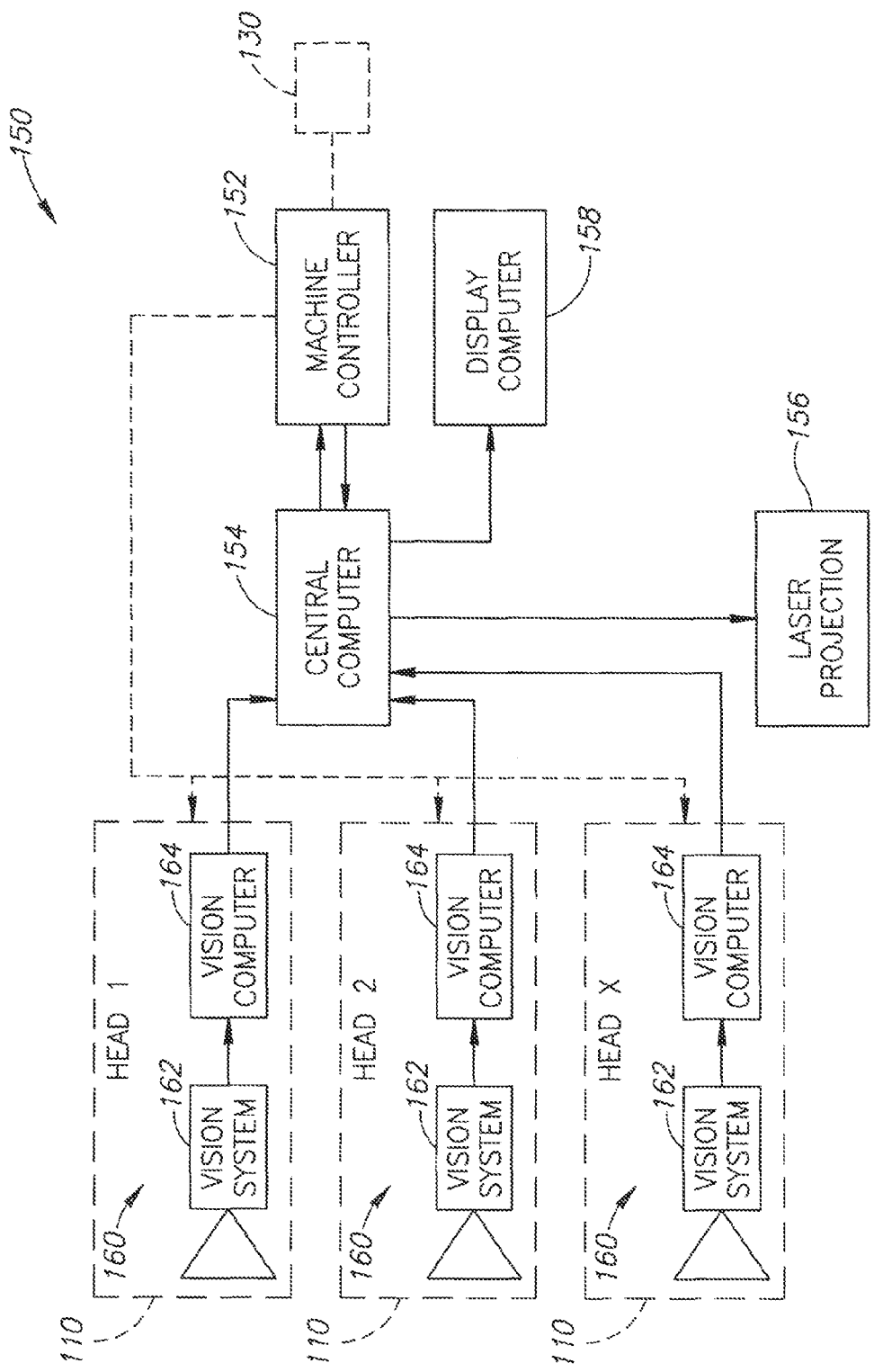
FIG. 2 is an illustration of an inspection system of the manufacturing system of FIG. 1.

FIG. 2 illustrates a control system 150 of the manufacturing system 100 of FIG. 1. The control system 150 includes a machine controller 152 operatively coupled to the translation platform 130 and to the head assemblies 110. The machine controller 152 is adapted to implement a control code that transmits control signals to the translation platform 130 and the head assemblies 110. The control signals command the movement and functions of the translation platform 130 and the head assemblies 110, thereby causing automated (or semi-automated) manufacturing of the laminated composite workpiece 142 on the forming tool 140. In the embodiment shown in FIG. 1, the manufacturing system 100 is of a type known as a multi-head tape lamination machine (MHTLM). In one specific embodiment, the system 100 includes eight head assemblies 110 for the placement of composite tape, however, in alternate embodiments, any desired number of head assemblies 110 may be employed.

Figure 3:
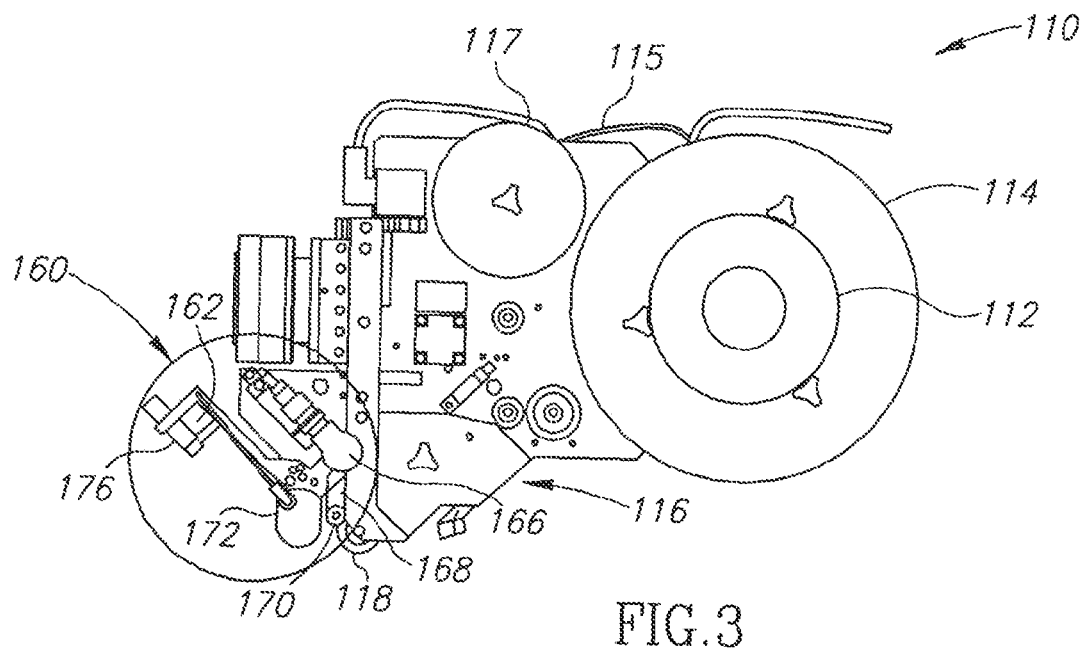
FIG. 3 is an illustration of a head assembly of the manufacturing system of FIG. 1.
Figure 4:
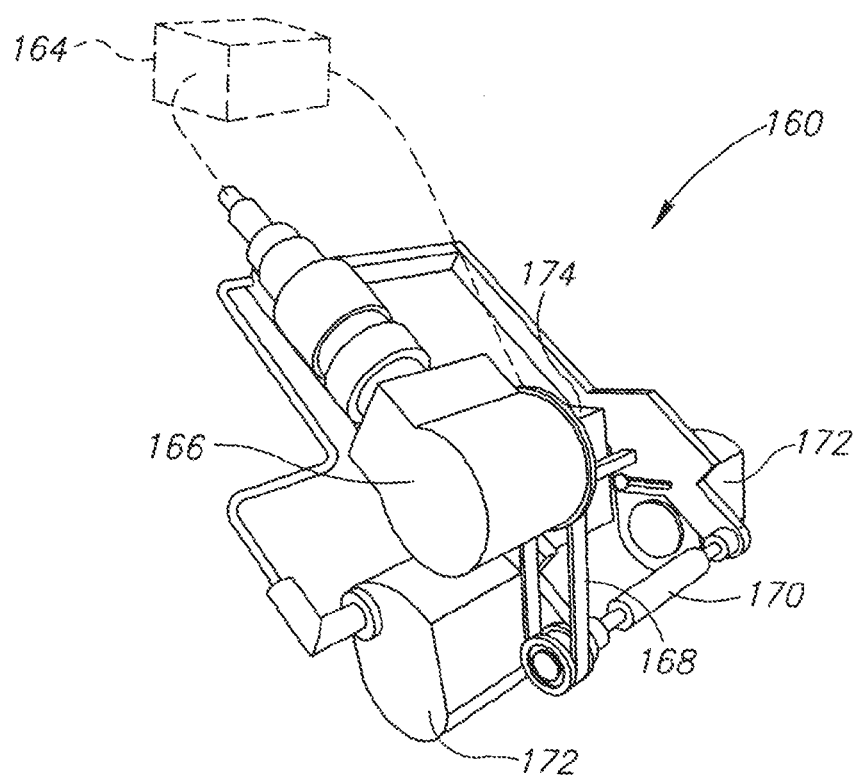
FIG. 4 is an illustration of a vision unit of the manufacturing system of FIG. 1.

FIG. 3 illustrates the head assembly 110 of the manufacturing system 100 of FIG. 1. The head assembly 110 includes a spindle 112 adapted to retain a roll 114 of a fiber-reinforced composite tape 115, and a feed assembly 116 adapted to receive, guide, feed, and apply the tape 115 from the roll 114 onto the workpiece 142. More specifically, the feed assembly 116 includes a feed roller 117 that receives the tape 115 from the roll 114, and a compaction roller 118 that applies and compresses the tape 115 onto the workpiece 142. The feed assembly 116 may include a variety of other components (e.g. motors, rollers, guides, sensors, etc.) adapted to cooperatively receive, feed, and guide the tape 115 from the roll 114 to the compaction roller 118, as described more fully, for example, in U.S. Pat. No. 6,799,619 B2 issued to Holmes et al., and U.S. Pat. No. 6,871,684 B2 issued to Engelbart et al., as well as in U.S. Publication No. 20030102070.

The head assembly 110 further includes a vision unit 160 adapted to perform in-process inspections of the manufacturing processes (in this case, composite tape application processes) performed by the head assembly 110.

Figure 6:
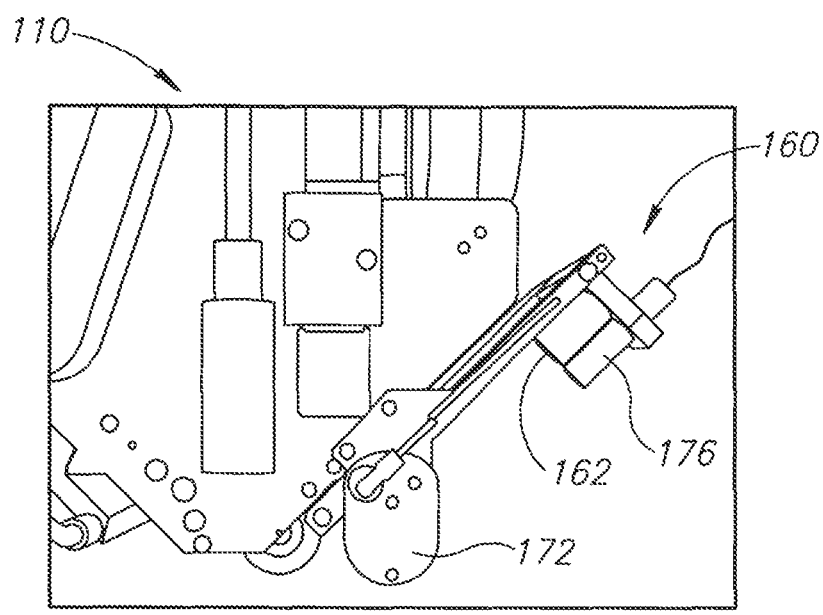
FIG. 6 is an illustration of the vision unit of FIG. 4.
Figure 7:
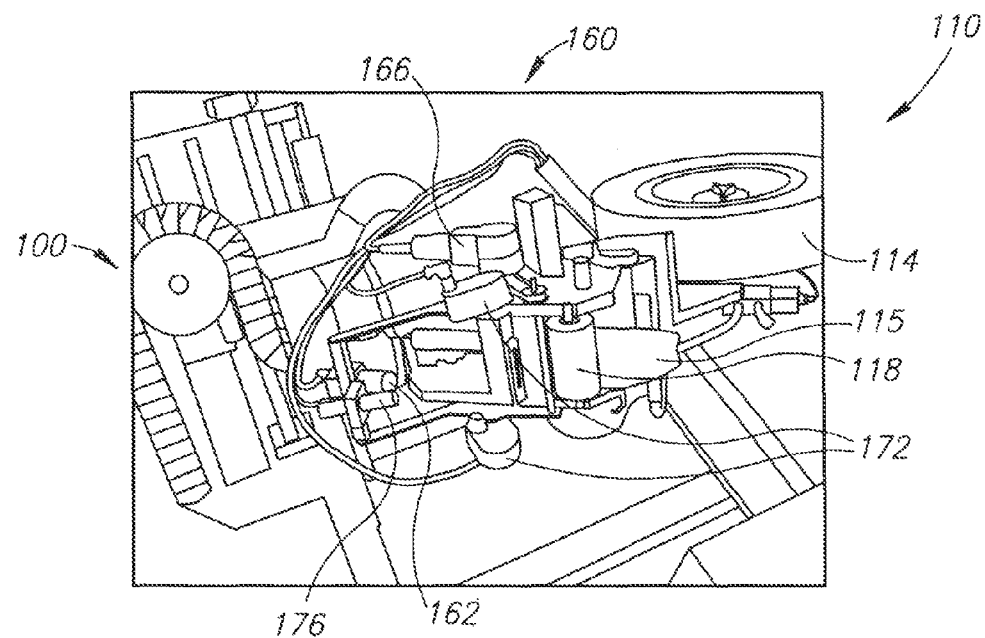
FIG. 7 is an illustration of a portion of the manufacturing system including the head assembly of FIG. 3.
Figure 8:
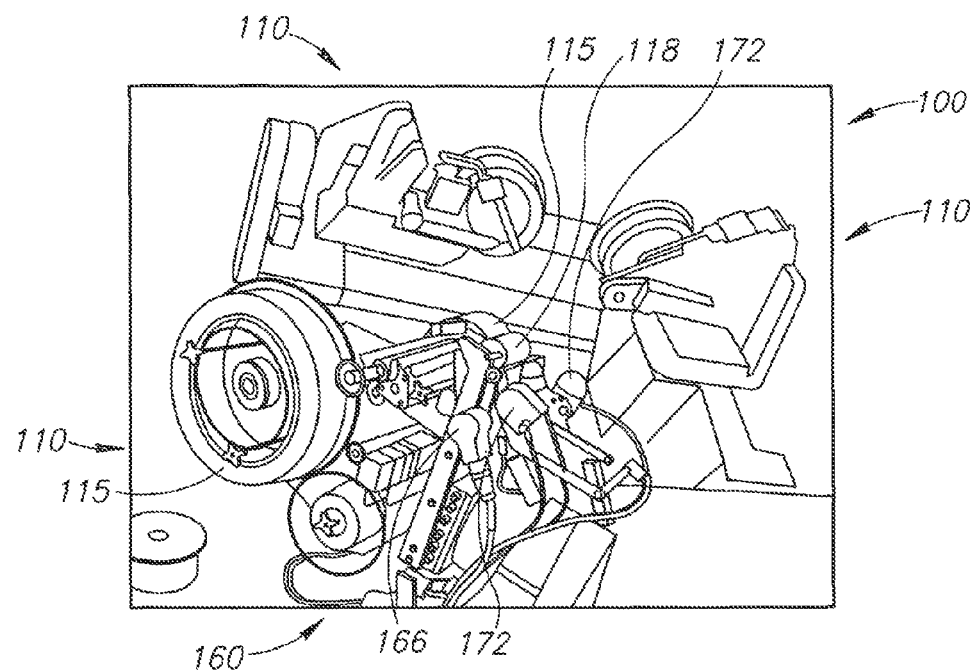
FIG. 8 is an illustration of a portion of the manufacturing system including the head assembly of FIG. 3.

As best shown in FIGS. 3 and 6, the vision unit 160 includes a camera 162 operatively positioned to view an area proximate the compaction roller 118 that includes the tape 114 as it is being applied and compressed onto the workpiece 142. A vision computer (or other suitable processor) 164 is coupled to the camera 162 and is adapted to acquire and analyze an image provided by the camera 162 for irregularities. The vision computer 164 may, for example, be adapted to analyze the image to determine whether any possible irregularities or errors are present in the image, and make accept/reject decisions based on one or more predetermined criteria stored within the vision computer 164 or otherwise entered through a user interface, as described more fully below.

As shown in FIG. 2, each vision computer 164 is coupled to a central computer 154 which, in turn, is coupled to the machine controller 152. Communication between the vision units 160 and the central computer 154 may be accomplished by standard Ethernet connections, or alternately, by a custom network or server. Communication may also be achieved through a wireless network that utilizes spread spectrum RF to overcome sources of interference in a typical factory environment.

Figure 5:
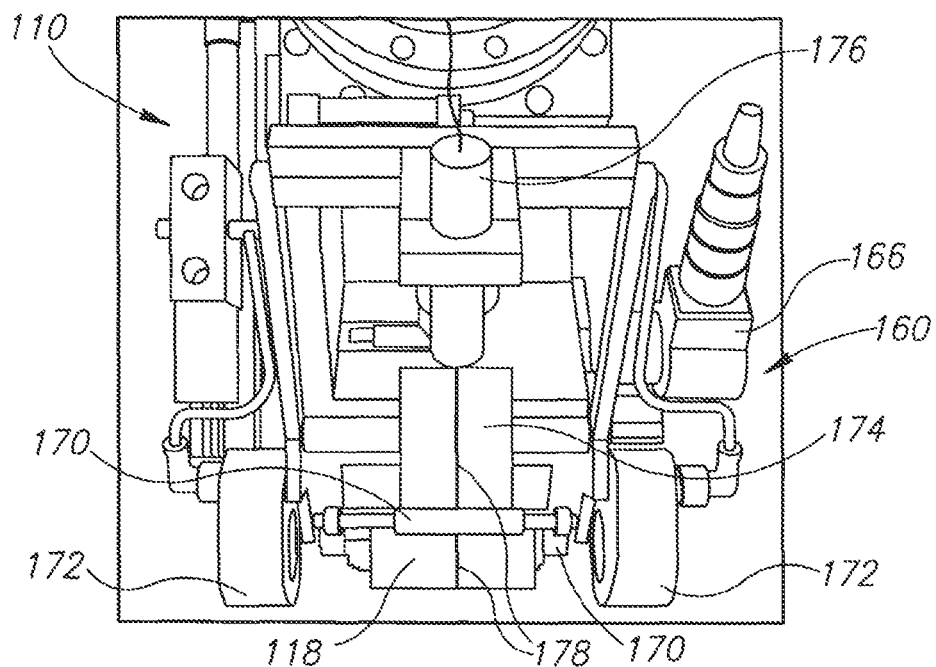
FIG. 5 is an illustration of the vision unit of FIG. 4.

With continued reference to FIGS. 4-8, the vision unit 160 also includes an encoder 166 that is driven by a drive belt 168 coupled to an encoder drive 170. The encoder drive 170 operatively engages the compaction roller 118 so that as the compaction roller 118 rolls along the workpiece 142, the encoder drive 170 drives the encoder 166 via the drive belt 168. The encoder 166 provides position information to the vision computer 164 for coordinating the location of possible irregularities indicated by the vision computer 164. As best shown in FIG. 5, two lighting sources 172 are laterally arranged on opposing sides of the encoder drive 170 for illuminating the area proximate the compaction roller 118 that is viewed by the camera 162. A mirror 174 is centrally disposed between the lighting sources 172 and is positioned proximate the compaction roller 118, and a laser 176 is positioned to project a laser line 178 through a portion of the area that is viewed by the camera 162. The mirror 174 may be operatively positioned to enable the camera 162 to simultaneously image the tape 114 that is being placed by the compaction roller 118 as well as to detect change in the laser line 178 projected from the laser 176.

In operation, as the head assemblies 110 are operated to apply the composite tape 115 onto the workpiece 142, the vision computers 164 monitor the application process, analyze the images in real time for possible manufacturing irregularities, and transmit the results of their image analyses to the central computer 154. As noted above, each vision computer 164 may be adapted to analyze the image to determine whether any possible irregularities are present in the image, and make accept/reject decisions. The vision computer 164 may use a variety of suitable methods and algorithms for determining whether irregularities are present in the image, and for making the accept/reject decisions, including, for example, those methods and algorithms disclosed in U.S. Pat. No. 6,871,684 issued to Engelbart et al. on Mar. 29, 2005, as well as those methods and algorithms disclosed in the following commonly-owned patents and applications, incorporated herein by reference: U.S. Pat. No. 7,171,033 by Engelbart et al., U.S. patent application Ser. No. 10/628,691 filed on Jul. 28, 2003, U.S. Pat. No. 7,289,656 by Engelbart et al., U.S. Pat. No. 7,424,902 by Engelbart et al., and U.S. Patent Publication No. 20060108048 by Engelbart et al. U.S. patent application Ser. No. 10/628,691 was abandoned, but a continuation thereof (U.S. patent application Ser. No. 10/846,974) issued as U.S. Pat. No. 7,236,625.

Figure 10:
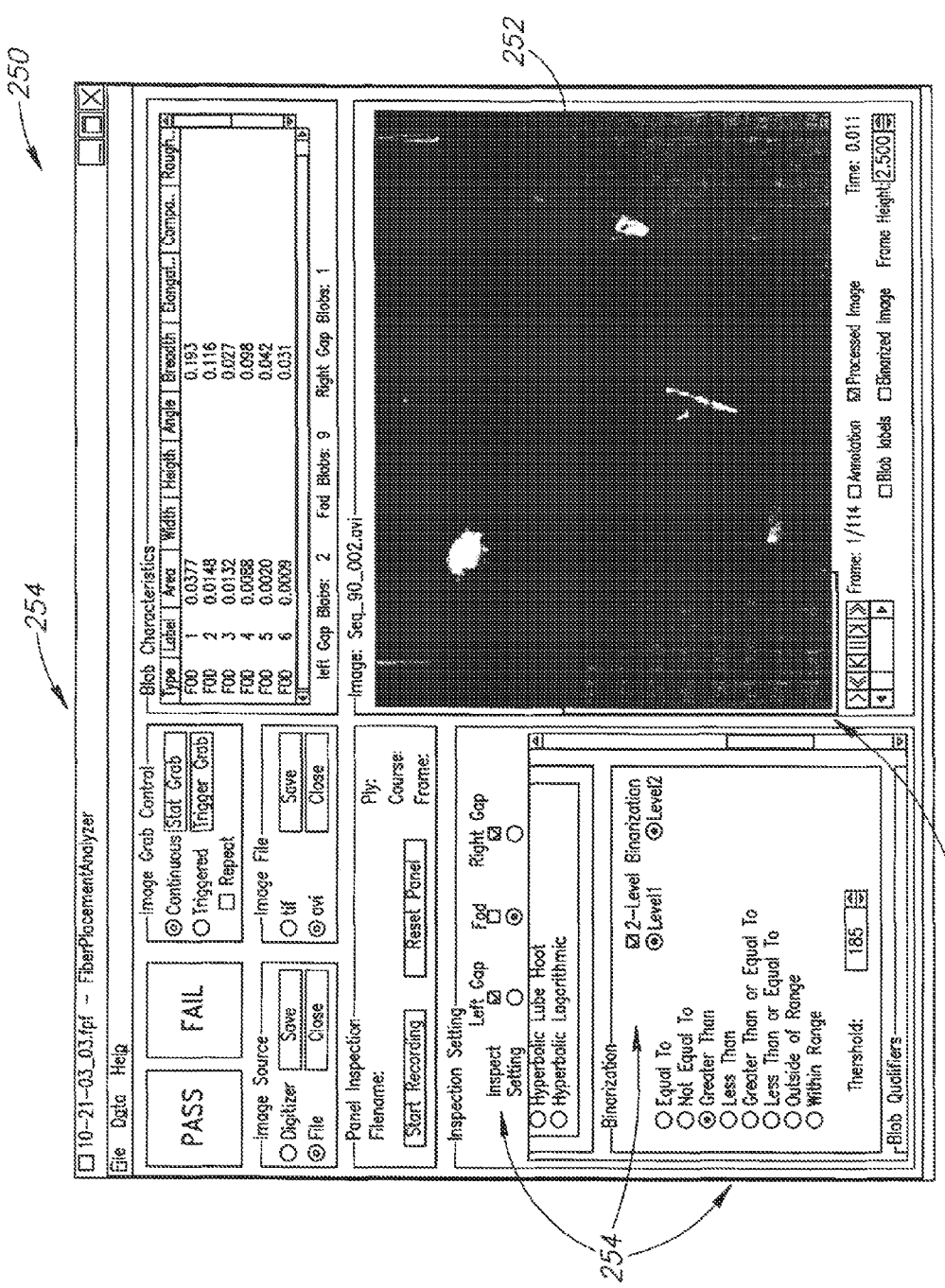
FIG. 10 is an illustration of a representative image provided by the vision unit of FIG. 4.

In one embodiment, the vision computers 164 transmit analysis results that indicate a possible manufacturing irregularity to the central computer 154, but do not transmit analysis results if no manufacturing irregularities are indicated. Alternately, the central computer 154 may receive and maintain a running display of images (both with and without possible irregularities) as seen through the camera 162 of the vision unit 160. For multiple head assemblies 110, this may be accomplished by a split screen display that shows the view from each head assembly 110 simultaneously in discrete windows. It may also be done by displaying each head assembly 110 view individually through selection of that head assembly 110 from a list (e.g. as shown in FIG. 10).

Upon receipt of irregularity information, the central computer 154 may query the machine controller 152 for the coordinates (e.g. x-y coordinates) of the possible irregularity, and may also receive position information from the encoder 166. The central computer 154 may then write the information regarding irregularities perceived by the vision computers 164 to a system error file 200, and may archive the corresponding images from the vision computers 164.

Figure 9:
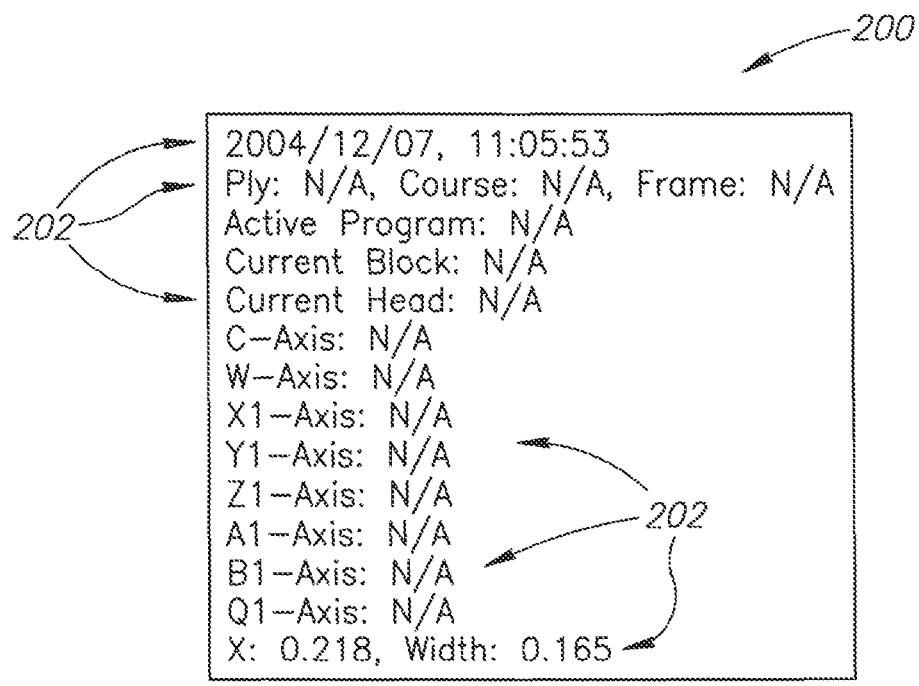
FIG. 9 is an illustration of a system error file produced by the manufacturing system of FIG. 1.

FIG. 9 illustrates a representative system error file 200 produced by the central computer 154. In this embodiment, the system error file 200 includes a plurality of error file entries 202, which provide various information regarding the possible irregularity location (e.g. date, time, ply, course, frame, active program, current block, current head, coordinate information from the machine controller 152, position information from the encoder 166, etc.). In one particular embodiment, the central computer 154 maintains a running list of irregularity locations by machine coordinates, and at the end of each completed ply (or layer), the central computer 154 sends the running list to a laser projection system 156. As shown in FIGS. 1 and 2, the laser projection system 156 may receive the information regarding possible irregularities from the central computer 154, and may project an irregularity identifier 157 onto the workpiece 142. The laser projection system 156 may include a processor that converts the machine coordinates for the purpose of locating and marking possible irregularities for detailed inspection and possible repair. The laser projection system 156 may be any suitable projection system, including those projection systems disclosed, for example, in U.S. Pat. No. 7,193,696.

The central computer 154 may also archive the corresponding images from the vision computers 164, as well as the related error file entries 202, and make them available for subsequent viewing and inspection on a display device 158 (FIG. 2). The display device 158 may be driven by the central computer 154, or alternately, a secondary computer may be used to run the display device 158 in order to maintain the processing speed of the central computer 154 for data archiving tasks.

In one embodiment, the images of possible irregularity locations from the vision computers 164 are provided to the display device 158 by selecting an appropriate error file entry 202 from the error file 200. For example, FIG. 10 is a representative screenshot 250 from the display device 158 that includes an image 252 provided by the vision unit 160 of FIG. 4. The screenshot 250 also includes a plurality of identifying data 254 corresponding to the error file entries 202 which provide information regarding the possible irregularity location. In this embodiment, a list 256 of head assemblies 110 is provided, allowing the image from each head assembly 110 to be viewed individually by selection of that head assembly 110 (e.g. Head 3) from the list 256.

The overall operation of the manufacturing system 100 will now be described with reference to FIGS. 11 through 14. The method 300 includes positioning the head assembly 110 proximate the forming tool 140 at a block 302, initiating operation of the head assembly 110 at a block 304, and initiating movement of the head assembly 110 using the translation platform 130 at a block 306. At a block 308, the fiber-reinforced composite tape 115 is applied to the forming tool 140 (or to the previously-applied layers of the workpiece 142).

Figure 11:
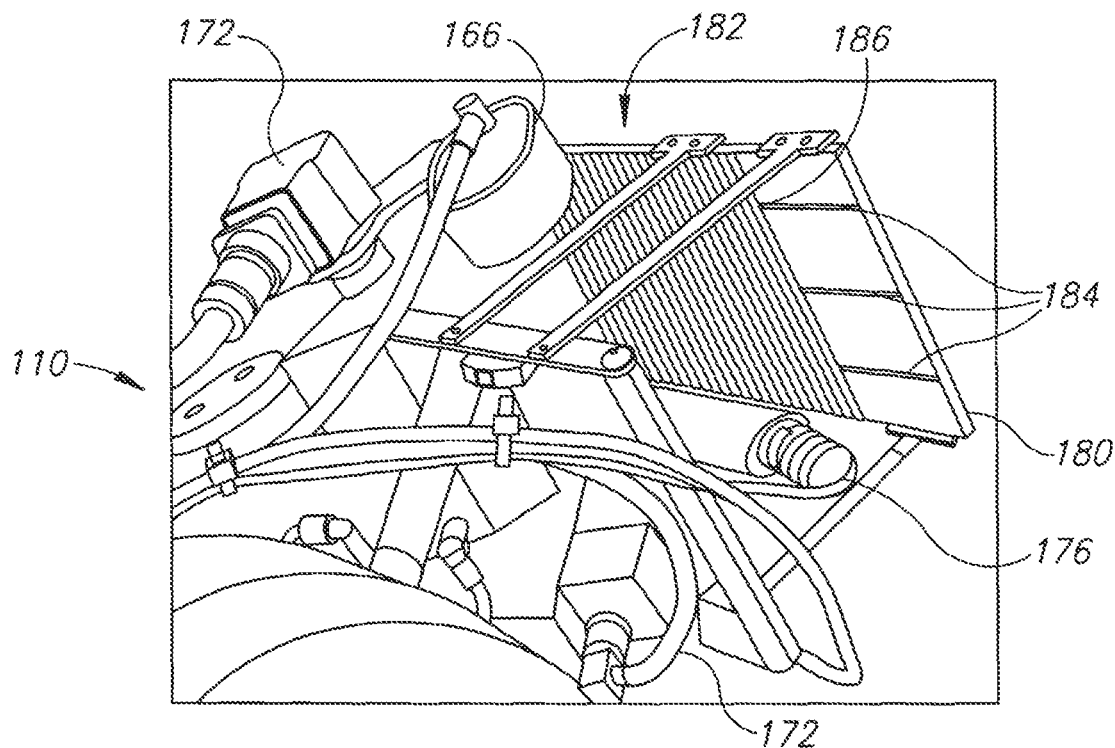
FIGS. 11 and 12 are illustrations of the manufacturing system in first and second modes of operation in conjunction with a calibration plate.
Figure 12:
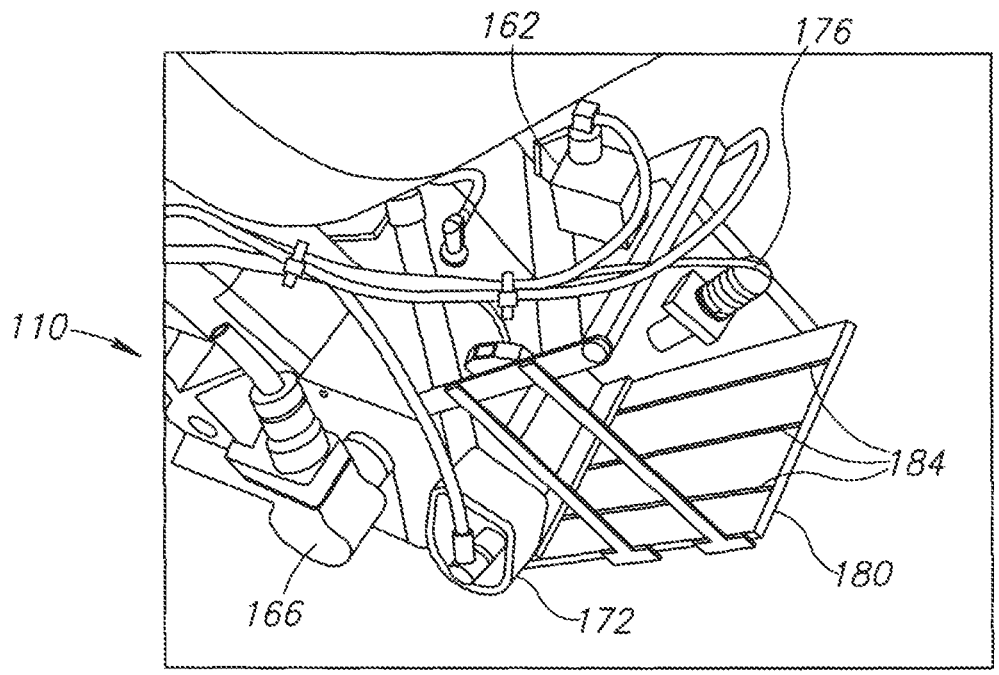
Figure 13:
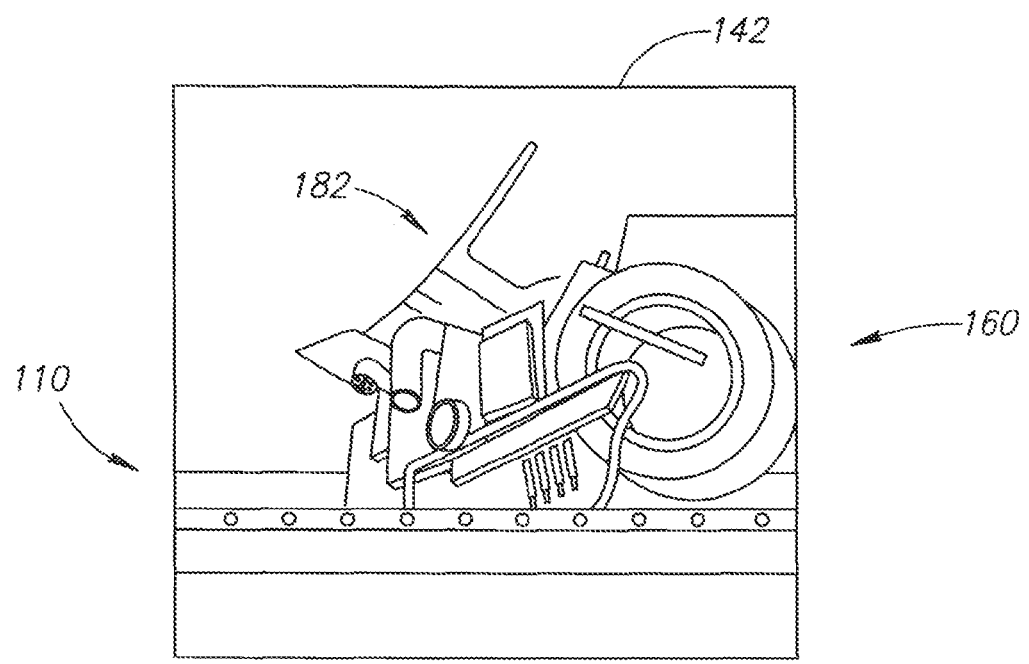
FIG. 13 is an illustration of the manufacturing system in operation on the workpiece of FIG. 1.

At a block 310, inspections are performed with the vision unit 160 simultaneously with the application of the tape (block 308). More specifically, in a first mode of operation, the vision unit 160 is operated in a laser striping mode to detect gaps between a recently-applied portion of the tape and a previously-applied portion of the tape. As described more fully in the above-referenced issued patents and pending patent applications, in the laser striping mode of operation, the beam from the laser 176 is conditioned by a lens system to form a plurality of lateral stripes 182. As shown in FIG. 11, the lateral stripes 182 are projected onto at least part of the area monitored by the camera 162. In the example shown in FIG. 11, the lateral stripes 182 are projected onto the calibration plate 180, however, during actual manufacturing operations, the lateral stripes 182 are projected onto the workpiece 142, as shown in FIG. 13. A plurality of calibration grooves 184 are formed in the surface of the calibration plate 180 (FIGS. 11 and 12). When the lateral stripes 182 intersect with one of the grooves 184, a discontinuity (or jog, or gap indication) 186 in the lateral stripe 182 becomes apparent. Similarly, on the workpiece 142, gaps which may occur between a recently-applied portion of the tape and a previously-applied portion of the tape also appear as gap indications 186. During actual manufacturing operations, such gap indications 186 are detected by the vision computer 164 during analysis of the images acquired by the camera 162, and corresponding error messages are generated to indicate that a gap has been detected.

Alternately, during the inspections performed using the vision unit 160 (block 310), irregularities (including foreign objects and debris (FOD)) may be detected using a second or "illumination" mode of operation. Again, as described more fully in the above-referenced issued patents and pending patent applications, in the illumination mode of operation, the lighting sources 172 are activated to brightly illuminate the area monitored by the camera 162. For example, FIG. 12 shows the lighting sources 172 operating in the illumination mode of operation on the calibration plate 180. The vision computer 164 analyzes the resulting images for discontinuities in reflected light intensity, and determines whether irregularities (e.g. bumps, ripples, etc.) are present on the calibration plate 180 (or on the workpiece 142) based on one or more predetermined criteria. The one or more predetermined criteria may, for example, be defined in terms of a presumed area. Any detected discontinuities in reflected light intensity having an area that meets or exceeds the presumed area may be classified as irregularities, and a corresponding error indicator message may be returned by the vision computer 164.

Figure 14:
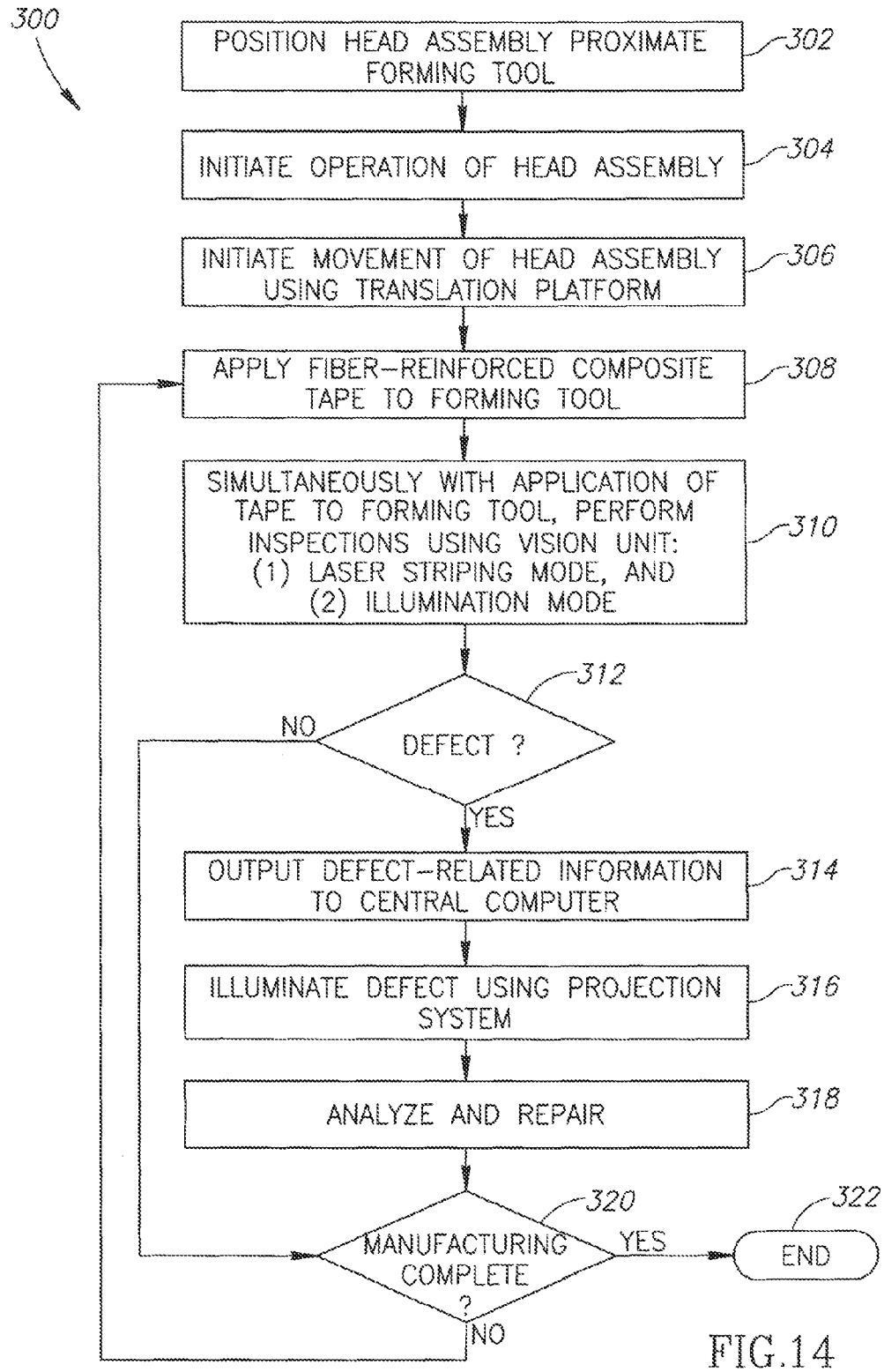
FIG. 14 is an illustration of a method of performing manufacturing operations.

With continued reference to FIG. 14, at a determination block 312, the method 300 determines whether the inspections performed using the vision unit (block 310) resulted in the detection of an irregularity. If not, the method 300 proceeds to the determination block 320 to determine whether manufacturing operations are complete. If manufacturing operations are not complete, the method 300 returns to the block 308 and continues the application of the fiber-reinforced composite tape, and the performance of the inspections (block 310), and repeats these operations as needed.

Alternately, if an irregularity is determined at the block 312, then at a block 314, the irregularity-related information is output to the central computer 154 (FIG. 2). At a block 316, the projection system 156 may be used to illuminate the area of the possible irregularity, and at a block 318, the area of the possible irregularity may be further inspected, analyzed, and repaired if necessary. The method 300 then proceeds to the determination block 320 to determine whether manufacturing operations are complete, and if not, the method 300 returns to the block 308 and continues the application of the fiber-reinforced composite tape, and the performance of the inspections (block 310), and repeats these operations as needed. If manufacturing operations are complete, then the method 300 terminates at the block 322.

Embodiments of systems and methods herein may provide significant advantages over prior systems and methods. For example, because the head assembly 110 includes its own dedicated vision unit 160 for performing inspections, in-process inspections may be performed simultaneously on different regions of the workpiece 142 as the head assemblies 110 are simultaneously performing manufacturing operations. The vision units 160 advantageously reduce downtime of the manufacturing system 100 by reducing or eliminating the need to shift inspection hardware between head assemblies 110. Also, because the central computer 154 has been relieved of the tasks of image acquisition, image analysis, and decision making by the vision computers 164, the central computer 154 is able to perform other tasks (e.g. archival tasks) relatively more rapidly in order to keep pace with the speed of material placement and inspection by the head assemblies 110.

It will be appreciated that a variety of embodiments in accordance with the present invention may be conceived, and that the invention is not limited to the particular embodiments described above and shown in the accompanying figures. For example, in alternate embodiments, the functions of the central computer 154 and the machine controller 152 (FIG. 2) may be combined into a single computer. Similarly, the display 158 may be integrated with the central computer 154 or with the machine controller 152. Of course, a variety of other embodiments may be conceived by combining various other components.

Furthermore, embodiments herein may be used in a wide variety of manufacturing applications for manufacturing a wide variety of components for a wide variety of products. For example, in the manufacturing system 100 shown in FIG. 1, the forming tool 140 is adapted for forming an elongated, tubular workpiece 142. In one specific embodiment, the workpiece 142 is a fuselage portion of an airplane, such as the 787 passenger aircraft commercially-available from The Boeing Company of Chicago, Ill. It will be appreciated, however, that alternate embodiments of the invention may be employed for the manufacture of composite components for a variety of other products, including other components for commercial and military aircraft, rotary wing aircraft, missiles or other types of flight vehicles, as well as components for boats, automobiles, trucks and other types of terrestrial vehicles, and any other desired structures.

Furthermore, although the disclosed embodiments have been described as being adapted for the application and collation of fiber-reinforced composite tape, it may be appreciated that in alternate embodiments, head assemblies having vision inspection units herein may be equipped with other types of tools for performing other types of manufacturing operations. For example, in alternate embodiments, assemblies may include riveters, welders, wrenches, clamps, sanders, nailers, screw guns, mechanical and electromagnetic dent pullers, and virtually any other desired type of manufacturing tools and measuring instruments.

The invention claimed is:
1. A system comprising:
a feed assembly for applying composite tape;

a unit for forming lateral stripes across a portion of the tape that has been applied;

a camera for capturing images of the lateral stripes; and a processor programmed to process the images of the lateral stripes to identify any discontinuities in the tape, wherein those stripes intersecting any discontinuities will make those discontinuities apparent.

2. The system of claim 1, wherein the unit includes a laser for generating a beam, and optics for conditioning the beam into the lateral stripes.

3. The system of claim 1, wherein the feed assembly, the unit, and the camera are included in a head assembly.

4. The system of claim 3, wherein the processor is also included in the head assembly.

5. The system of claim 1, wherein the feed assembly includes a compaction roller, and wherein the camera is positioned proximate the compaction roller to view the tape as the tape is being applied and compressed.

6. The system of claim 5, further comprising an encoder engaged with the compaction roller to indicate position coordinates of any discontinuities.

7. The system of claim 6, further comprising a projection system configured to receive the coordinates from the encoder and project identifiers onto the applied tape at any detected discontinuities.

8. The system of claim 7, wherein the processor processes the images in real time and projects the identifier for visual inspection while the tape is being applied.

9. The system of claim 6, wherein the camera captures the images at regular intervals that are triggered by the encoder.

10. The system of claim 6, further comprising a central computer programmed to enter position coordinates of a detected discontinuity into an error log.

11. The system of claim 1, further comprising a translation platform for systematically moving the feed assembly along a translation path.

12. The system of claim 11, wherein the translation platform includes a controller adapted to command movement and function of the translation platform and the feed assembly to perform at least one of automated and semi-automated manufacturing operations.

13. The system of claim 1, wherein the processor is programmed to detect a gap between a recently-applied portion of the tape and a previously-applied portion of the tape.

14. The system of claim 1, wherein the processor identifies discontinuities without performing edge analysis.

15. A tape lamination machine comprising:

a forming tool; and a plurality of head assemblies for depositing composite tape on the forming tool, each head assembly including a feed assembly for applying composite tape, a unit for forming lateral stripes across a portion of the tape that has been applied, a camera for capturing images of the lateral stripes, and a processor programmed to process the images of the stripes to identify any discontinuities in the tape, wherein those stripes intersecting any discontinuities will make those discontinuities apparent.

16. The machine of claim 15, wherein each of the plurality of head assemblies is used to apply and compress the tape, and also perform dedicated image analysis and discontinuity detection.

17. The machine of claim 15, further comprising a translation platform for systematically moving each head assembly along a translation path proximate the workpiece.

18. The machine of claim 15, wherein each processor is programmed to detect a gap between a recently-applied portion of tape and a previously-applied portion of tape.

19. The machine of claim 15, wherein each head assembly includes an encoder for indicate position coordinates of any discontinuities.

20. The machine of claim 19, further comprising a projection system configured to receive the position coordinates from the encoder and project identifiers onto the applied tape at any detected discontinuities.

* * * * *